United States Patent
Brown et al.

(10) Patent No.: US 9,812,282 B2
(45) Date of Patent: Nov. 7, 2017

(54) SYSTEM AND METHOD FOR IRRADIATING A PRODUCT

(71) Applicant: MEVEX CORPORATION, Stittsville (CA)

(72) Inventors: Peter W. A. Brown, Almonte (CA); David A. Brown, Dunrobin (CA); David J. Hepworth, Ottawa (CA); David Macrillo, Almonte (CA)

(73) Assignee: Mevex Corporation, Stittsville (CA)

( * ) Notice: Subject to any disclaimer, the term of this patent is extended or adjusted under 35 U.S.C. 154(b) by 0 days.

(21) Appl. No.: 14/952,986

(22) Filed: Nov. 26, 2015

(65) Prior Publication Data

US 2017/0154751 A1    Jun. 1, 2017

(51) Int. Cl.
  *A61L 2/08* (2006.01)
  *H01J 37/141* (2006.01)

(52) U.S. Cl.
  CPC ............ *H01J 37/141* (2013.01); *A61L 2/087* (2013.01)

(58) Field of Classification Search
  CPC .... H01J 37/141; H01J 37/147; H01J 2237/31; H01J 37/20; H01J 3/027; H01J 3/08; A61L 2/087; A61L 2202/23; A61L 2202/122; A61L 2/08; A61L 2/24; A61L 2202/14; A61L 2/007; G21K 5/04; G21K 5/10
  See application file for complete search history.

(56) References Cited

U.S. PATENT DOCUMENTS

| | | | | |
|---|---|---|---|---|
| 3,358,239 A * | 12/1967 | Siegfried | ............... | G21K 1/093 |
| | | | | 250/354.1 |
| 4,434,372 A * | 2/1984 | Cleland | ................... | B29C 35/08 |
| | | | | 250/400 |
| 4,492,873 A * | 1/1985 | Dmitriev | ................... | G21K 5/04 |
| | | | | 219/121.29 |
| 5,172,401 A * | 12/1992 | Asari | ...................... | H01J 35/14 |
| | | | | 378/10 |
| 5,528,658 A * | 6/1996 | Hell | ........................ | H01J 35/30 |
| | | | | 378/121 |
| 5,548,630 A * | 8/1996 | Hell | ........................ | A61B 6/032 |
| | | | | 378/121 |
| 5,847,401 A * | 12/1998 | McKeown | ............... | G21K 5/04 |
| | | | | 250/396 ML |
| 6,683,319 B1 * | 1/2004 | Koenck | ..................... | G21K 5/10 |
| | | | | 250/396 R |
| 8,618,521 B2 * | 12/2013 | Loo | ...................... | A61N 5/1065 |
| | | | | 250/492.1 |

(Continued)

*Primary Examiner* — Wyatt Stoffa
(74) *Attorney, Agent, or Firm* — Borden Ladner Gervais LLP; Louis B. Allard

(57) ABSTRACT

An electron beam from an accelerator is injected into a vacuum chamber and bent approximately 90 degrees by an electromagnet, which can be translated along the vacuum chamber and along the propagation direction of the electron beam. Under the influence of the electromagnet, electrons exit the scan chamber through a thin metal vacuum barrier and are directed toward the product to be irradiated. There can be an x-ray converter located between the electron beam and the product. As the electromagnet moves along the scan chamber and along the direction of the electron beam, the bending angle of the electron beam can be adjusted as a function of the position of the electromagnet with respect to the product.

11 Claims, 10 Drawing Sheets

(56) References Cited

U.S. PATENT DOCUMENTS

| | | | |
|---|---|---|---|
| 9,018,603 B2* | 4/2015 | Loo | A61N 5/1065 250/492.1 |
| 2002/0162971 A1* | 11/2002 | Koenck | A23B 4/015 250/455.11 |
| 2004/0079900 A1* | 4/2004 | Korenev | G21K 5/10 250/492.3 |
| 2004/0113094 A1* | 6/2004 | Lyons | G21K 5/10 250/435 |
| 2005/0178977 A1* | 8/2005 | Koenck | A23B 4/015 250/455.11 |
| 2008/0116390 A1* | 5/2008 | Gordon | A61L 2/082 250/396 ML |
| 2008/0198970 A1 | 8/2008 | Kirshner et al. | |
| 2008/0251156 A1* | 10/2008 | Kang | A01M 1/226 144/335 |
| 2010/0270477 A1* | 10/2010 | Nishino | A61L 2/087 250/455.11 |
| 2011/0006225 A1* | 1/2011 | Fletcher | A61L 2/087 250/492.3 |
| 2011/0092759 A1* | 4/2011 | Koubychine Merkulov | A61N 5/10 600/1 |
| 2011/0198513 A1* | 8/2011 | Holm | A61L 2/087 250/492.3 |
| 2011/0210263 A1* | 9/2011 | Abs | A61L 2/087 250/396 ML |
| 2012/0145929 A1* | 6/2012 | Nishino | A61L 2/087 250/492.3 |
| 2012/0217390 A1* | 8/2012 | Luxich | G01T 1/08 250/305 |
| 2013/0231516 A1* | 9/2013 | Loo | A61N 5/1065 600/1 |
| 2014/0027651 A1* | 1/2014 | Kawasaki | A61L 2/08 250/453.11 |
| 2014/0299786 A1* | 10/2014 | Yokobayashi | B65G 47/847 250/455.11 |
| 2014/0350324 A1* | 11/2014 | Iwata | A61N 5/10 600/1 |
| 2015/0108366 A1* | 4/2015 | Kawasaki | G21K 5/04 250/453.11 |
| 2015/0123005 A1* | 5/2015 | Abs | A61L 2/087 250/396 ML |
| 2015/0284907 A1* | 10/2015 | Medoff | H01J 33/04 250/453.11 |
| 2016/0083131 A1* | 3/2016 | Yokobayashi | A61L 2/087 250/454.11 |
| 2016/0310764 A1* | 10/2016 | Bharadwaj | A61N 5/1078 |

* cited by examiner

SYSTEM AND METHOD FOR IRRADIATING A PRODUCT

FIELD

The present disclosure relates generally to a system and method for irradiating products. In particular, the present disclosure relates to a system and method that uses an electromagnet to steer particles generated by a particle accelerator toward the product to be irradiated.

BACKGROUND

Throughout the history of using ionizing radiation (IR) for processing products, many variations of delivering ionizing radiation dose to the products have been developed and improved with respect to efficiency in the delivery of ionizing radiation, regardless of the means of producing the ionizing radiation. The impetus to improve this efficiency is driven by the high cost of generating IR and by the demand for higher rates of processing.

Delivery of a minimum ionizing radiation dose is required to ensure efficacy of the irradiation process. The ability to maintain the ionizing radiation dose below a maximum value is also generally required to avoid damage to the processed product or to remain below a prescribed regulatory maximum ionizing radiation dose. The ratio of maximum ionizing radiation dose to minimum ionizing radiation dose is referred to as the dose uniformity ratio (DUR). DUR and overall efficiency are closely related although efficiency also depends on aspects of delivery to the surfaces of materials being processed. Ideally, the DUR would be equal to 1.0; larger values indicate some waste of ionizing radiation.

Improvements in systems and methods for irradiating products are desirable.

SUMMARY

In a first aspect, the present disclosure provides a system for irradiating a product. The system comprises an electron accelerator; a vacuum chamber, the electron accelerator configured to inject electrons into the vacuum chamber; an electromagnet movable along an axis of the vacuum chamber, the electromagnet having a coil assembly, the electromagnet to generate a magnetic field in the vacuum chamber, the magnetic field being a function of an electric current circulating in the coil assembly; a position controller to control a position of the electromagnet along the axis of the vacuum chamber; a current controller to control the electric current circulating in the coil assembly, the position of the electromagnet and the electric current circulating in the coil assembly being selectable to have the electromagnet steer electrons from the vacuum chamber toward the product.

In a second aspect of the present disclosure, there is provided a method of irradiating a product. The method comprises: injecting, along an axis, electrons into a vacuum chamber; steering, away from the axis, with an electromagnet, the electrons towards the product; moving the electromagnet along the axis as the electrons are steered towards the product; and adjusting a steering angle of the electrons as a function of a position of the electromagnet with respect to the product.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Generally, the present disclosure provides a method and system for delivering ionizing radiation to products (for example, large pallets) in a uniform and efficient way. The method and system of the present disclosure improves on aspects of radiation processing of materials by reducing the wasted ionizing energy delivered to the surfaces of materials and also improved DUR.

The general idea is that the electron beam from the accelerator is injected into a vacuum chamber (scan chamber) and bent approximately 90 degrees (or any suitable angle) by an electromagnet which can be translated (moved) along the scanning chamber and along the propagation direction of the electron beam. The electromagnet may be mounted outside the vacuum system or inside the vacuum system. Under the influence of the electromagnet, electrons exit the scan chamber through a thin metal vacuum barrier (an electron window) and are directed toward the object to be irradiated. The object can be an x-ray converter or a product (for example, pallets loaded with produce or medical devices). As the electromagnet moves along the scan chamber and along the direction of the electron beam, the bending angle of the electron beam can be adjusted as a function of the position of the electromagnet with respect to the product. The adjustment of the bending angle as a function of the position of the electromagnet can be used to make the radiation beam convergent on the product in such a way as to improve the DUR and the processing efficiency.

Figure 1:
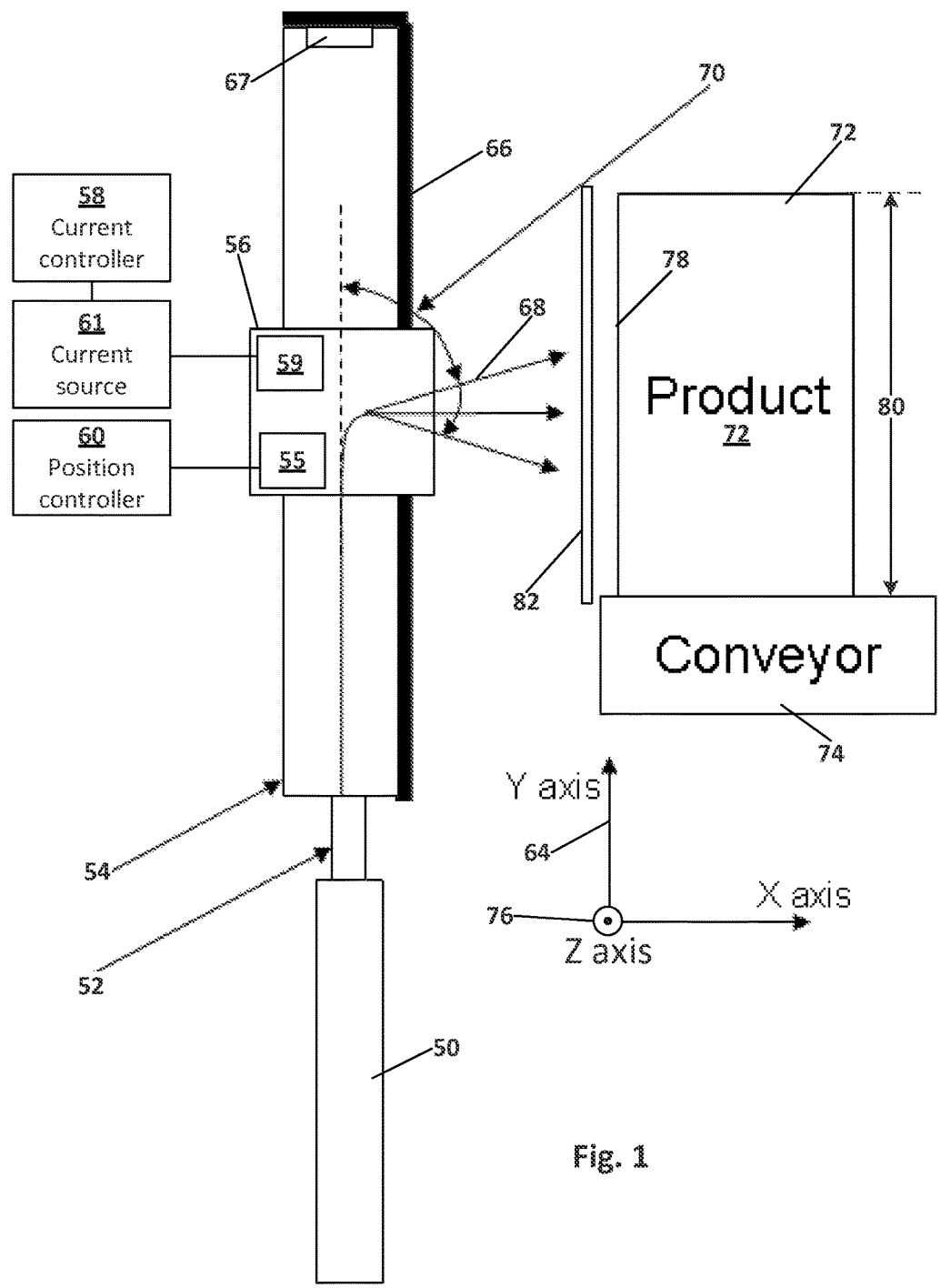
FIG. 1 shows a side elevation view of an embodiment of a system for irradiating a product in accordance with the present disclosure.

FIG. 1 shows a side elevation view of an embodiment of a system for irradiating a product in accordance with the present disclosure. The system comprises an electron accelerator 50, a drift tube 52, a vacuum chamber 54, and an electromagnet 56 connected to a translation assembly 55. The electron accelerator 50 is configured to emit electrons and to accelerate the electrons parallel to the Y-axis 64. The accelerated electrons form an electron beam. The vacuum chamber 54 is configured to receive the electron beam from the electron accelerator 50, through the drift tube 52. The electromagnet 56, when energized, can change the path of the electron beam to steer the electron beam away from the Y-axis 64 and towards a window 66 (also referred to as a vacuum window or an electron window), which is traversed by the electron beam. The electron beam is shown at reference numeral 68, after having traversed the window 66.

The electromagnet 56 comprises a coil assembly 59 that is connected to a current source 61. The angle 70 (can also be referred to as the steering angle) at which the electron beam 68 is output from the vacuum chamber 54 depends, amongst other factors, on the electrical current circulating the coil assembly 59. The electrical current circulating in the coil assembly is controlled by a current controller 58, which is connected to the current source 61. The position of the electromagnet 56 is controlled by a position controller 60 through the translation assembly 55. The translation assembly 55 can include any suitable device that can serve to displace, position, or both, the electromagnet 56. The device can be, for example, a linear transducer, a position encoder, or a position resolver.

The electron beam 68 is directed toward the product to be irradiated, namely, product 72. In an industrial setting, the product 72 can be secured to, or placed on, a conveyor 74 that moves the product 72 along a direction parallel to the Z-axis 76 to cause the product 72 to intercept the electron beam 72.

In cases where the electron beam 72 can be steered to span an angle that allows to irradiate the entire height 80 of the surface 78 of the product 72 with a target DUR, the electromagnet 56 can be fixedly positioned at a pre-determined position and the current circulating in the coil assembly 59 can be varied to cause the electron beam 68 to scan over the height 80 as the product is moved (conveyed) to intercept the electron beam 68. This allows the entire surface 78 to be irradiated.

In case where the height 80 of the product 72 is too tall to allow the electron beam to be scanned along the entire height 80, the angle of the electron beam 68 can be set to a fix value (for example, to have the electron beam 68 impinge on the surface 78 at an incidence angle of 0 degree) and the position controller 60 can control the translation assembly 55 to move the electromagnet 56 along the entire height 80 of the product 72. This can be done repeatedly as the product 72 is conveyed by the conveyor 74, to allow the entirety of the surface 78 to be irradiated.

In some embodiments, instead of the product 72 being irradiated by the electron beam 68, there can be a converter plate 82 located between the electromagnet 56 and the product 72. The converter plate 82 is selected to emit x-rays towards the product 72, in the same direction as the electron beam 68. The converter plate 82 can be made of any suitable material such as, for example, Tantalum or Titanium.

The system of FIG. 1 can also comprise a beam analyzer 67 located to receive the electron beam 68 upon the electron beam 68 being subjected to a null magnetic field. That is, the beam analyzer can be located directly opposite the electron beam source 50, when, for example, the coil assembly 59 of the electromagnet 55 draws no current. The beam analyzer 67 can measure, for example, the electron beam current and the beam energy. Alternatively, the beam analyzer 67 can be located at any other suitable location where the position of the electromagnet 55 and the current circulating in the coil assembly 59 can be adjusted to cause the electron beam to impinge on the beam analyzer 67 for analysis.

Figure 2:
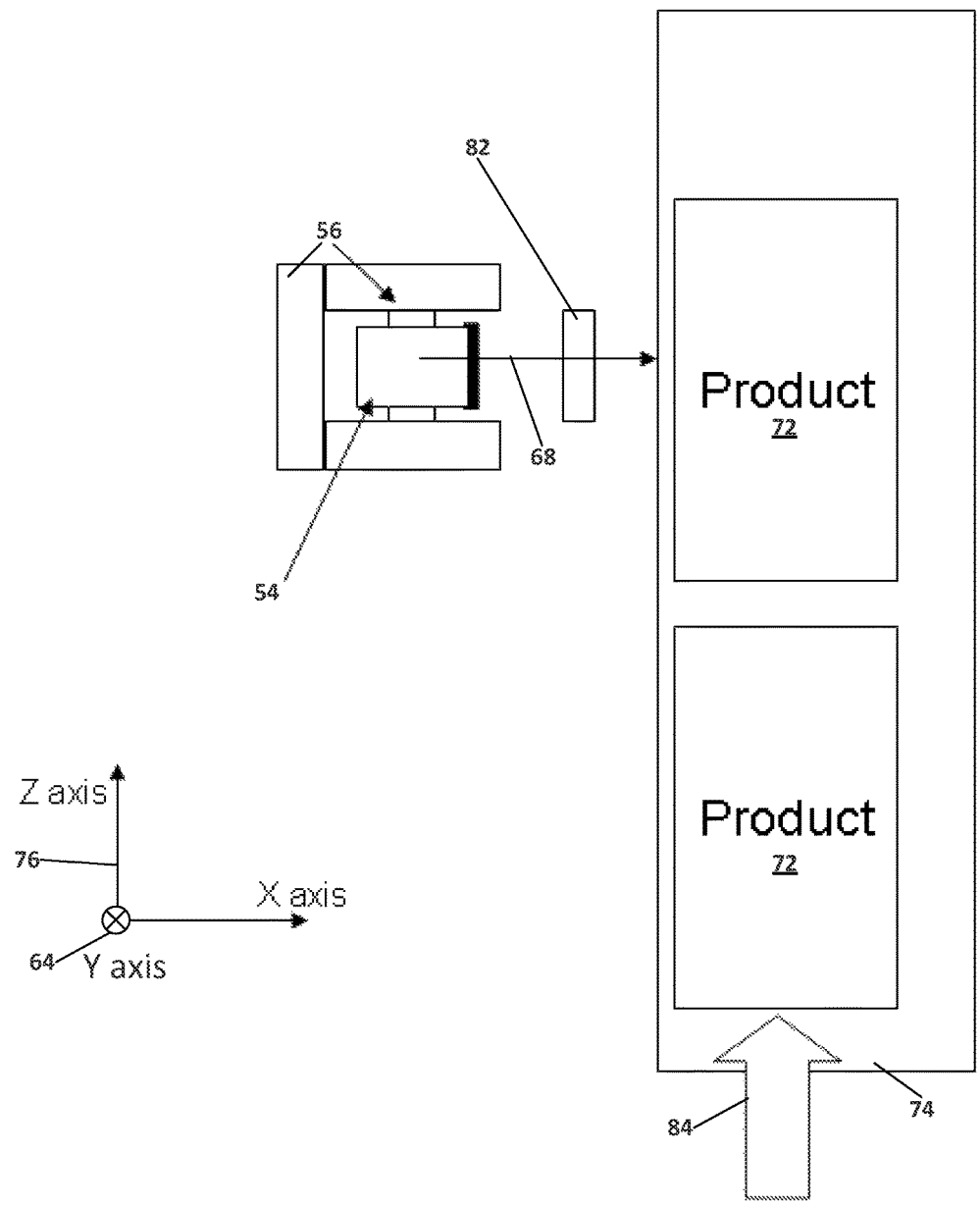
FIG. 2 shows a top view of the system of FIG. 1.
Figure 3:
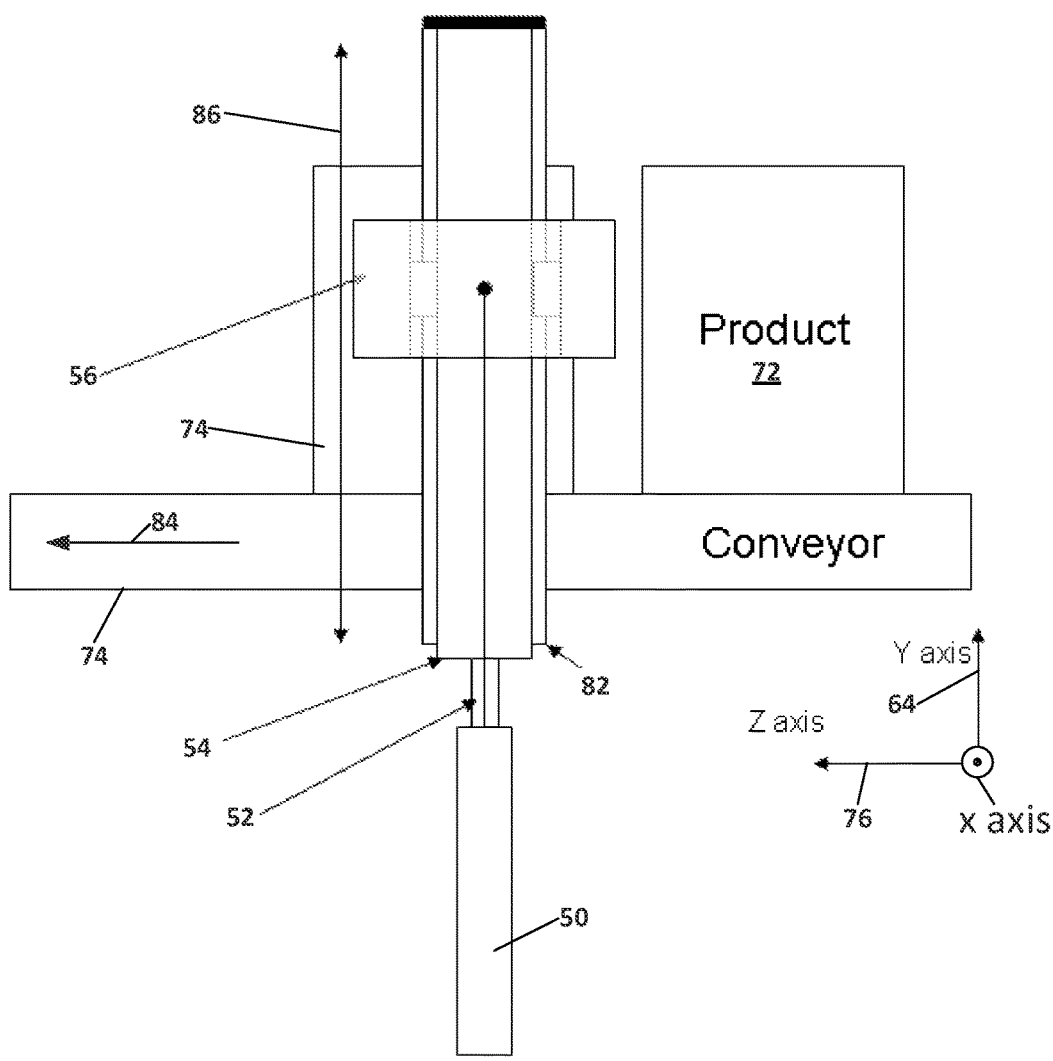
FIG. 3 shows another side elevation view of the system of FIG. 1.

FIG. 2 shows a top view of the system of FIG. 1. The arrow 84 indicates the direction in which the products 72 are being conveyed. FIG. 3 shows another side elevation view of the system of FIG. 1. The double arrow 86 indicates the direction in which the electromagnet can be moved.

In the system shown at FIGS. 1, 2 and 3, the electromagnet 56 is located outside the vacuum chamber 54. However, embodiments where the electromagnet is housed within the vacuum chamber 54 are also within the scope of the present disclosure.

Figure 4:
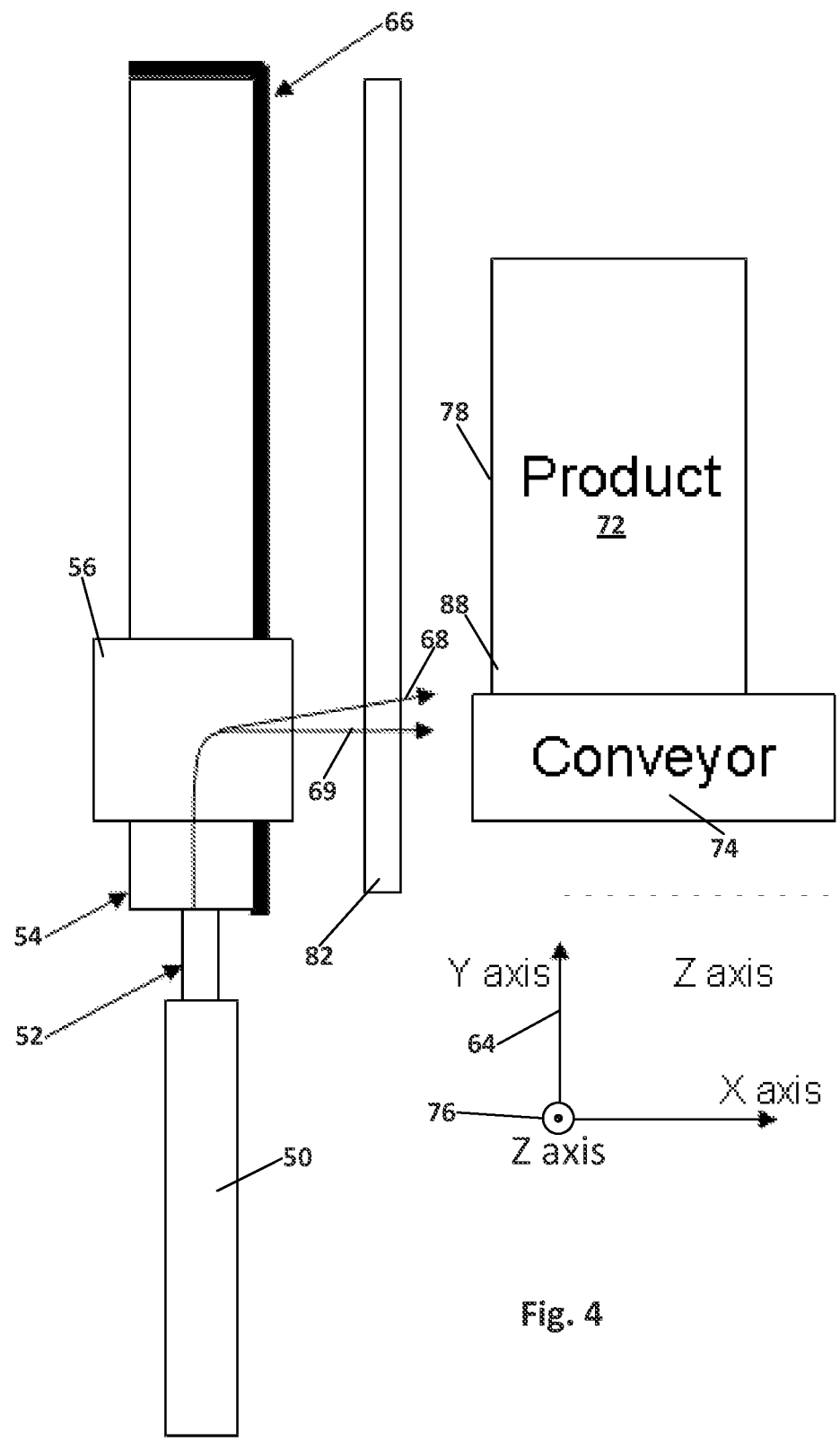
FIG. 4 shows the system of FIG. 1 but with the electromagnet positioned at a lower point along the Y-axis than in FIG. 1.
Figure 5:
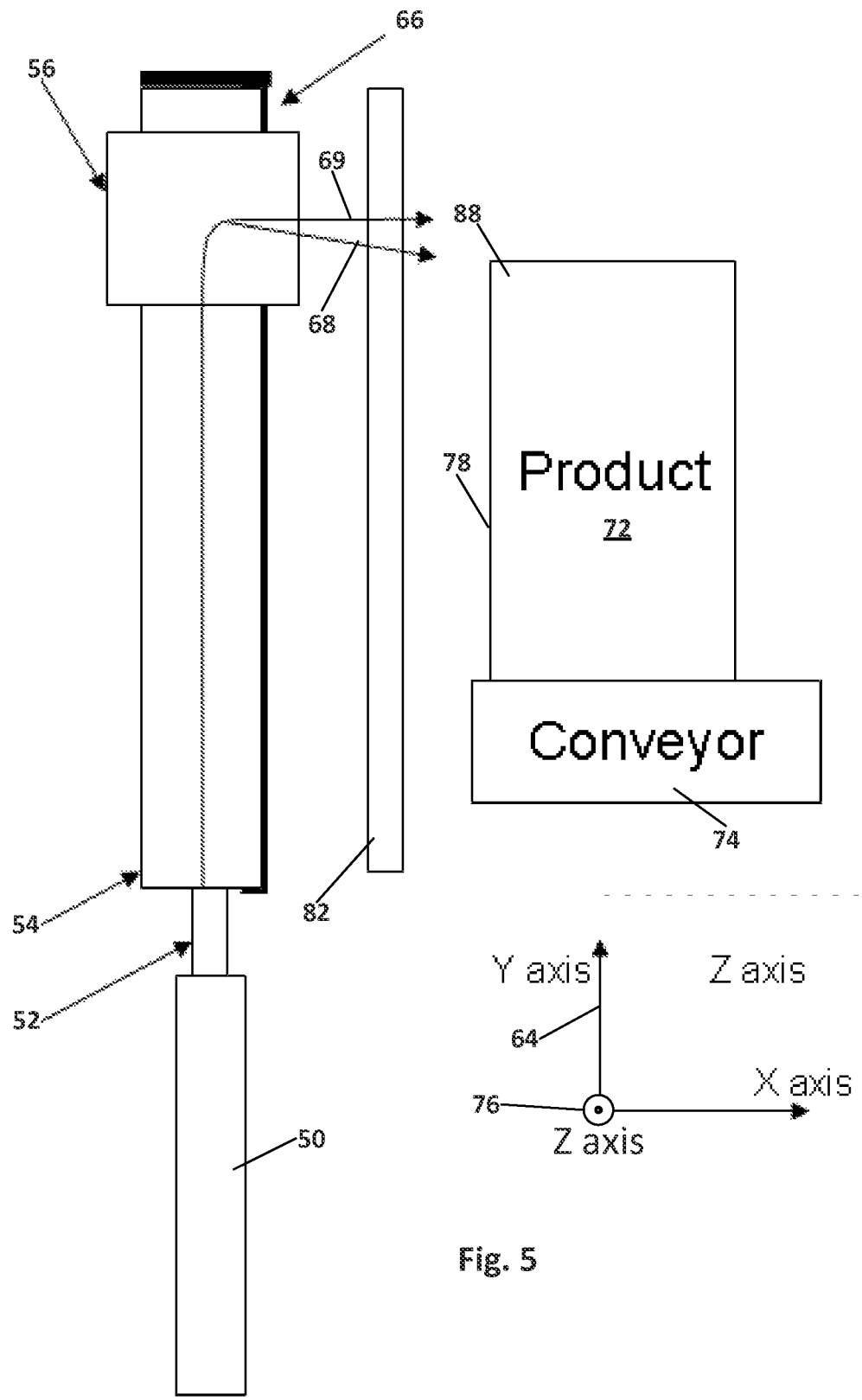
FIG. 5 shows the system of FIG. 1 but with the electromagnet positioned at a higher point along the Y-axis than in FIG. 1.

FIG. 4 shows the system of FIG. 1 but with the electromagnet 56 positioned at a lower point along the Y-axis 64 than in FIG. 1. FIG. 5 shows the system of FIG. 1 but with the electromagnet 56 positioned at a higher point along the Y-axis 64 than in FIG. 1. The adjustment of the angle of exit of the electron beam 68 from the electromagnet 56 can be varied as a function of the position of the electromagnet 56 along the Y-axis 64, in order to achieve the desired dose distribution to the product 72, as the product 72 is conveyed along the Z-axis 76, to intercept the electron beam 68. The speed at which the product 72 is conveyed can depend on the target irradiation dose of the product as well as on the target DUR and the intensity of the electron beam 68.

In FIG. 4, the electron beam 68 points upwards and the bending angle can be as little as 60 degrees (or any other suitable angle) when the vertical position of electromagnet 56 coincides with, or is close to, the bottom portion 88 of the product 72, as shown in this figure. Reference numeral 69 indicates the direction of an electron beam bend to 90 degrees. The bending angle of the electron beam can be augmented from 60 degrees to 90 degrees as the electromagnet 56 is moved to vary its vertical position to coincide with, or be close to, the middle of the height of the product 72, as shown at FIG. 1. The bending angle can be further augmented from 90 degrees to 150 degrees (or any other suitable angle) as the electromagnet 56 is moved to vary its vertical position to coincide with, or be close to, the top portion 90 of the product 72; this is shown in FIG. 5. As such, the angle of the electron beam 68 can be controlled, through the current controller 58 and the current source 61, to point towards the product 72 or, more specifically, toward the surface 78 of the product, for any vertical position of the electromagnet 56 with respect to the product 72.

In other embodiments, the bending angle can be varied as a function of the vertical position of the electromagnet 56 with respect to the product 72, to achieve an angle of incidence of the radiation beam on the product that produces a target irradiation dose distribution (profile) on the product (on the surface of the product that is irradiated).

The electromagnet 56 can be positioned at a prescribed position, along the scan chamber 54, and the bending angle can be varies the bending angle as function of time, and in relation to position of the product 72 along the Z-axis 76 as the product 72 is conveyed along the Z-axis. This allows for the efficient treatment of products much shorter than the maximum allowed product height.

The electromagnet 56 can include angled pole faces that defined a target focal length.

The system of the present disclosure allows the replacement of a Co-60 or CS-137 radiation source, in an existing gamma irradiation plant, with an electron accelerator and movable electromagnet.

The system of the present disclosure also allows installation of an electron accelerator and electromagnet in a new irradiation plant which was originally designed to be equipped with a gamma source.

Figure 6:
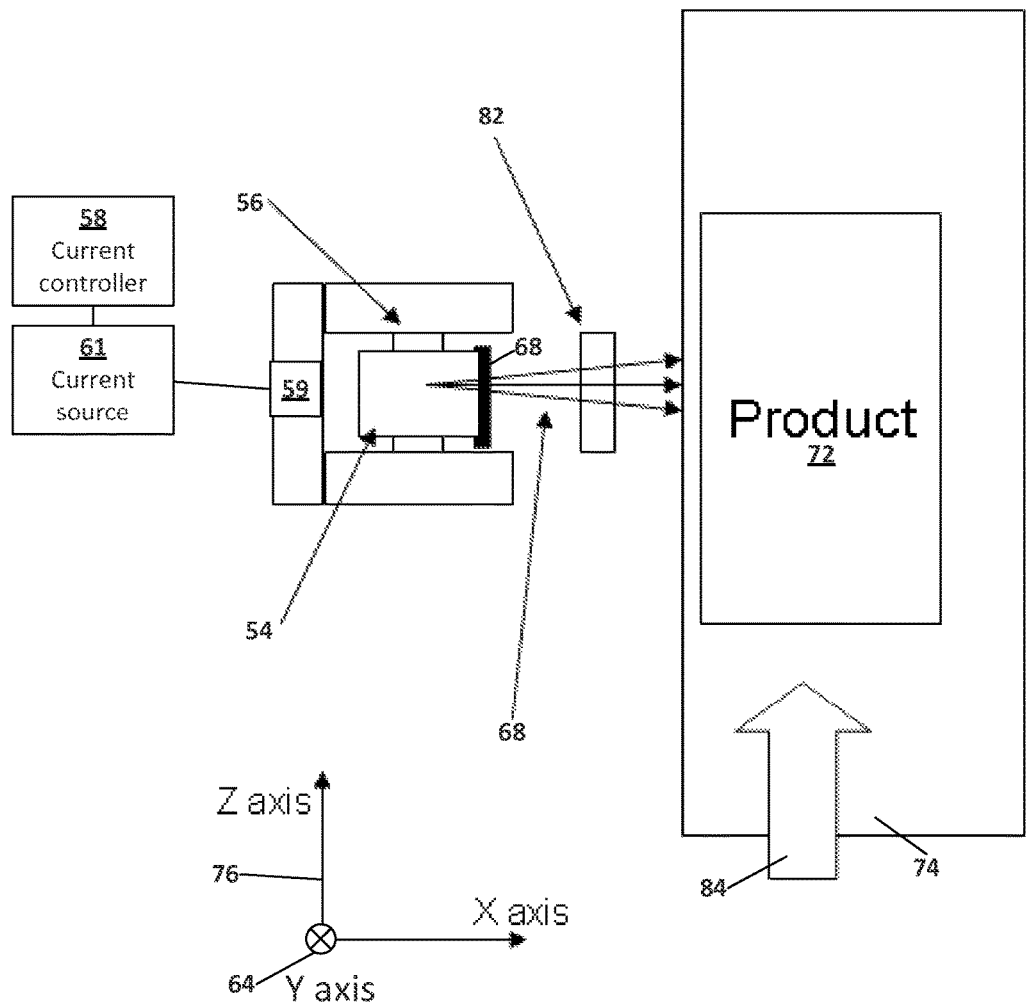
FIG. 6 shows a top view of the system of FIG. 1 but with the current controller controlling the current source to vary the electrical current in the coil assembly to cause the electron beam to move in the X-Z plane.

FIG. 6 shows a top view of the system of FIG. 1 but with the current controller 58 controlling the current source 61 to vary the electrical current in the coil assembly 59 to cause the electron beam 68 to move (wiggle, or side scan) in the X-Z plane. The "side scanning" of the electron beam 68 reduces the irradiation dose deposited in the window 66.

Figure 7:
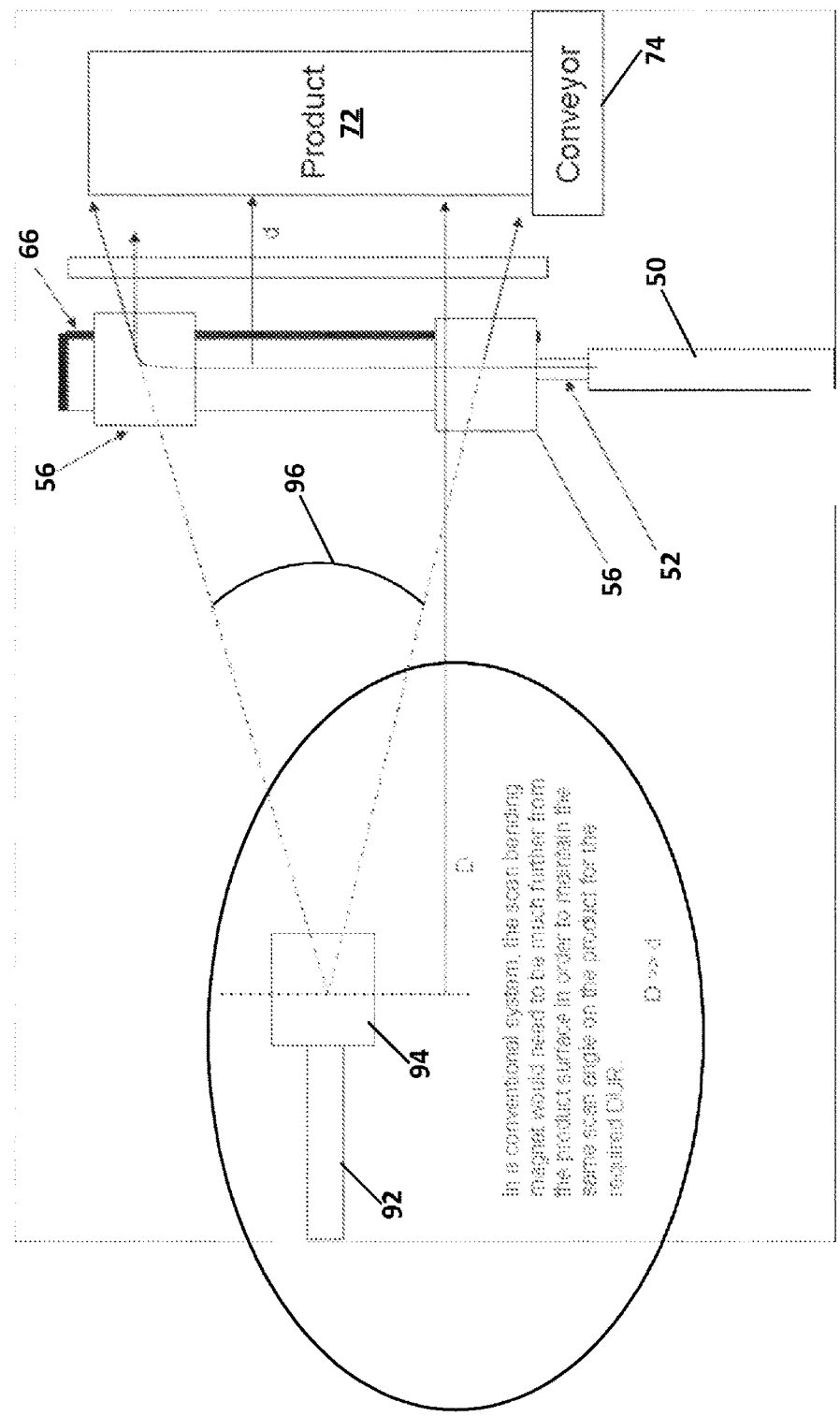
FIG. 7 shows a side view of the system of FIG. 1, with the electromagnet shown at two distinct vertical positions.

FIG. 7 shows a side view of the system of FIG. 1, with the electromagnet 56 shown at two distinct vertical positions (there is only one electromagnet in the system; it can be moved between the positions shown in this Figure). FIG. 7 also shows a conventional electron accelerator 92 coupled to an electromagnet 94. The electromagnet 94 is fixedly secured at a vertical position that coincides with the middle of the height of the product 72. As is known in the art, using a fixed electromagnet requires that the distance between the electromagnet center and the product to be at least twice that of the height of the product being treated in order to maintain the required DUR across the product. As evidenced by FIG. 7, the footprint penalty for having the electromagnet 94 secured as shown is considerable: the horizontal distance 'D' from the electromagnet 94 to the product 72 is much larger than the horizontal distance 'd' from the electromagnet 56 and the product 72. This comparison supposes that both electromagnets 56 and 59 can scan an electron beam within the same angle 96.

Figure 8:
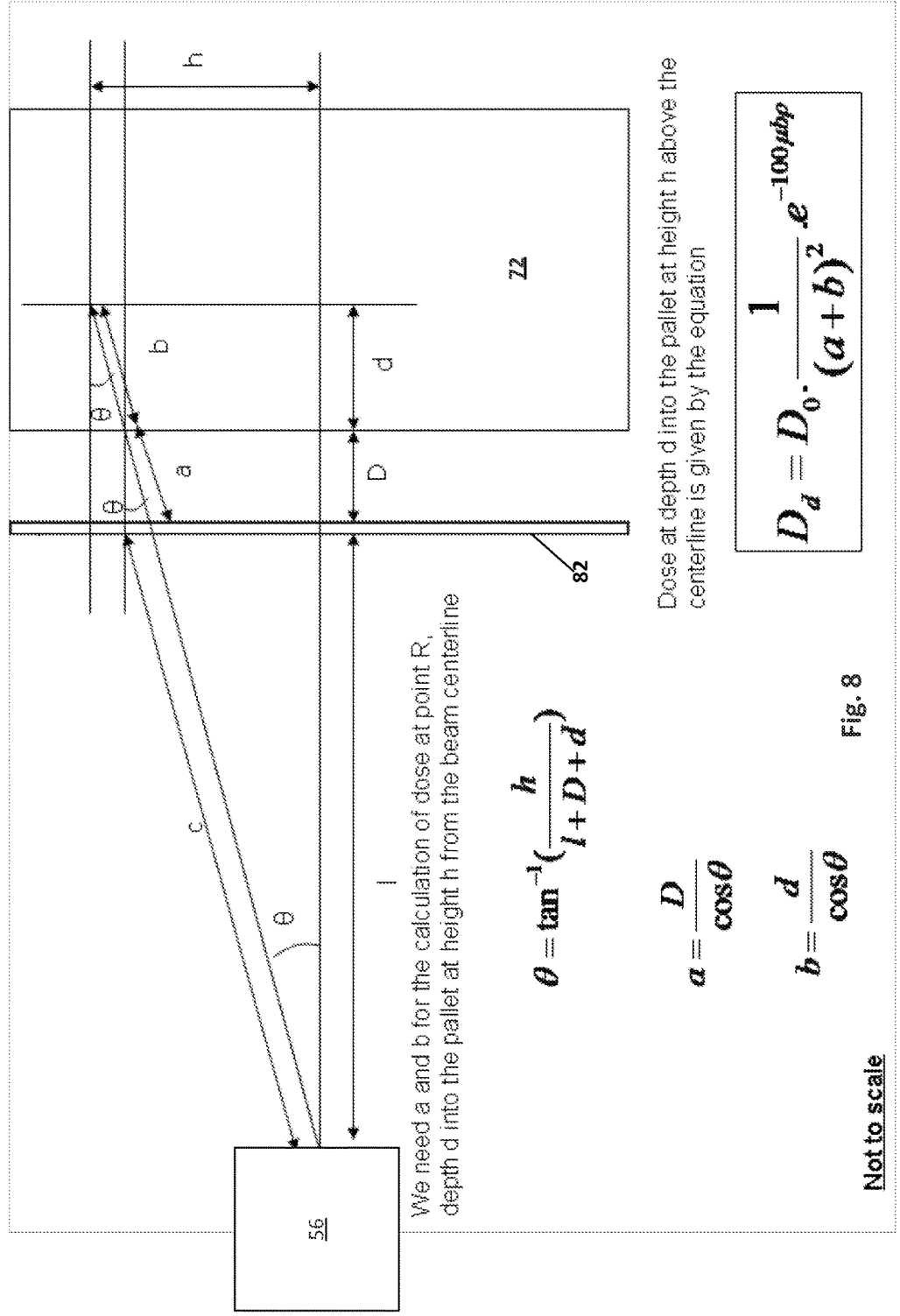
FIG. 8 shows a geometrical representation of the derivation of an equation for delivered irradiation dose.

FIG. 8 shows a geometrical representation of the derivation of the equation:

$$D_d = D_0 \times \frac{1}{(a+b)^2} \times e^{-100\mu b \rho}$$

where $\mu$ is the mean mass attenuation coefficient of the product and $\rho$ is the mean density of the product being irradiated.

Figure 9:
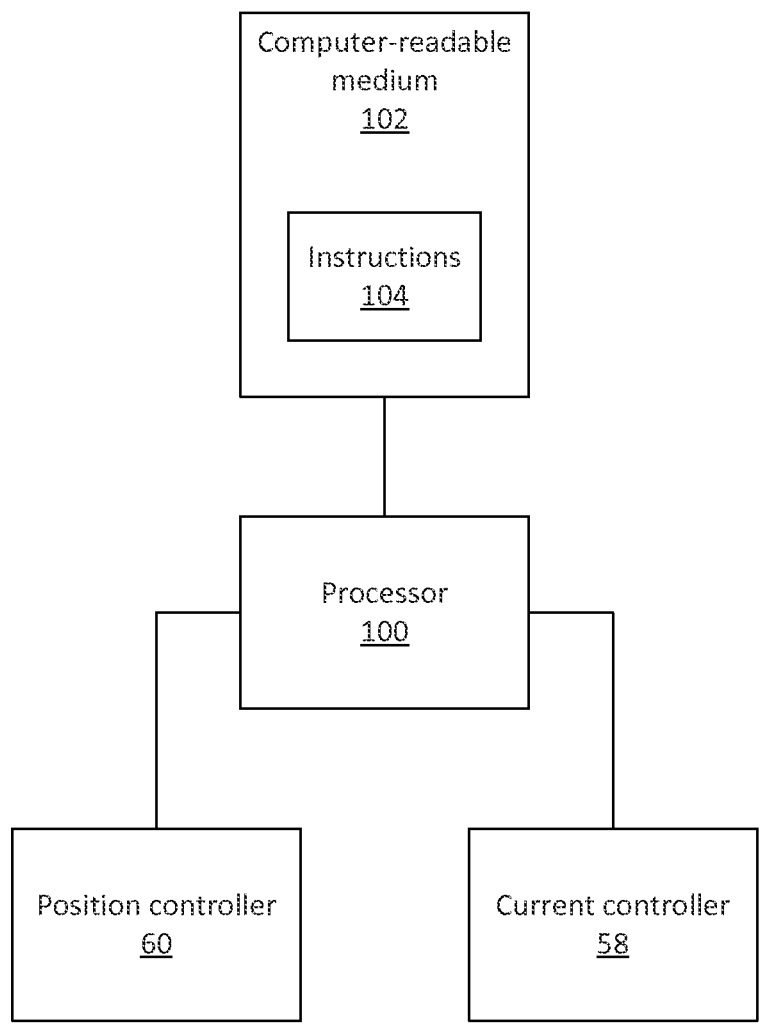
FIG. 9 shows a processor operationally connected to a position controller, a current controller, and a computer-readable medium.

FIG. 9 shows a processor 100 that is operationally connected to the position controller 60 and to the current controller 58. FIG. 9 further shows a tangible, non-transitory computer-readable medium 102 that has recorded thereon instructions 104 to be performed by the processor 100 to cause the position controller 60 to vary the position (vertical position) of the electromagnet 60 with respect to the product 72 and to cause the current controller 58 to vary the electric current circulating in the coil assembly 59 as a function of the position of the electromagnet 56 with respect to the product 72. The electric current can be varied to adjust, as a function of the vertical position of the electromagnet 56 with respect to the product 72, a steering angle of the electrons steered from the vacuum chamber toward the product.

Figure 10:
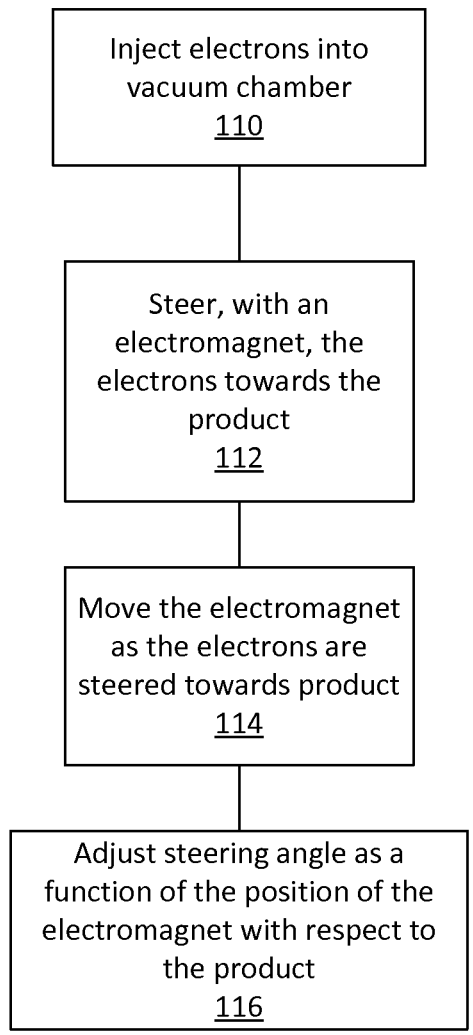
FIG. 10 shows a flowchart of an exemplary method in accordance with the present disclosure.

FIG. 10 shows a flowchart of an exemplary method of irradiating a product in accordance with the present disclosure. At step 110, electrons (a beam of electrons) are injected into a vacuum chamber, along an axis of the vacuum chamber. At action 112, the electrons are steered, with an electromagnet, away from the axis and towards the product to be irradiated. At action 114, the electromagnet is moved along the axis as the electrons are steered towards the product. At action 116, the steering angle of the electrons is adjusted as a function of a position of the electromagnet with respect to the product. The steering angle is shown in FIG. 1, at reference numeral 70. In FIG. 1, the axis along with the electrons are injected into the vacuum chamber is the Y-axis 64.

In the context of the present disclosure, elements can be said to be operationally connected to each other when, for example, a signal present in one element can be communicated to another element. Further, elements can be said to be operationally connected when an action in, or state of, one element can be controlled by, or related to, an action in, or a state of, another element.

The control software used to achieve the desirable result is part of the invention and its architecture allows the recording of all parameters affecting the dose delivered to the materials being processed. This feature allows the users of this invention to archive the treatment information, to link that information to each individual product, and retrieve for presentation.

This apparatus allows for compact treatment of large products such as pallets and the treatment of small products with the same electron scanning system without the usual compromises.

This invention will reveal a compact apparatus which achieves the desired goals of improved DUR and higher efficiency in utilization of IR by using a novel arrangement of magnetic beam deflection and mechanical positioning In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:
1. A system for irradiating a product, the system comprising:
an electron accelerator;
a vacuum chamber, the electron accelerator configured to inject electrons into the vacuum chamber;

an electromagnet movable along an axis of the vacuum chamber, the electromagnet having a coil assembly, the electromagnet to generate a magnetic field in the vacuum chamber, the magnetic field being a function of an electric current circulating in the coil assembly;

a position controller to control a position of the electromagnet along the axis of the vacuum chamber;

a current controller to control the electric current circulating in the coil assembly, the position of the electromagnet and the electric current circulating in the coil assembly being selectable to have the electromagnet steer electrons from the vacuum chamber toward the product;

a processor operationally connected to the position controller and to the current controller; and a tangible, non-transitory computer-readable medium having recorded thereon instructions to be performed by the processor to cause the position controller to vary the position of the electromagnet with respect to the product and to cause the current controller to vary the electric current circulating in the coil assembly as a function of the position of the electromagnet with respect to the product, the electric current being varied to adjust, as a function of the position of the electromagnet with respect to the product, a steering angle of the electrons steered from the vacuum chamber toward the product.

2. The system of claim 1 wherein the steering angle is also adjusted as a function of a target irradiation dose profile of the product.

3. A system for irradiating a product, the system comprising:

an electron accelerator;

a vacuum chamber, the electron accelerator configured to inject electrons into the vacuum chamber;

an electromagnet movable along an axis of the vacuum chamber, the electromagnet having a coil assembly, the electromagnet to generate a magnetic field in the vacuum chamber, the magnetic field being a function of an electric current circulating in the coil assembly;

a position controller to control a position of the electromagnet along the axis of the vacuum chamber;

a current controller to control the electric current circulating in the coil assembly, the position of the electromagnet and the electric current circulating in the coil assembly being selectable to have the electromagnet steer electrons from the vacuum chamber toward the product;

a processor operationally connected to the position controller and to the current controller; and a tangible, non-transitory computer-readable medium having recorded thereon instructions to be performed by the processor to cause the position controller to position the electromagnet with respect to the product to have the electromagnet and the product separated by a distance that is less or equal to a pre-determined distance and to cause the current controller to vary the electric current circulating in the coil assembly to steer, over an angle, the electrons from the vacuum chamber toward the product, a dimension of the product subtending the angle over which the electrons are steered.

4. The system of claim 3 wherein the dimension of the product is the height of the product.

5. The system of claim 1 wherein the position of the electromagnet and the electric current circulating in the coil assembly being further selected in accordance with energy imparted to the electrons by the electron accelerator.

6. The system of claim 1 further comprising a beam analyzer located in the vacuum chamber, the beam analyzer to analyze a beam of electrons propagating in the vacuum chamber.

7. The system of claim 1 wherein the electromagnet further has angled pole pieces, the angled poles pieces formed to define a focal length of the electromagnet.

8. The system according to claim 1 wherein the vacuum chamber includes a vacuum window through which electrons exit the vacuum chamber, the instructions to be performed by the processor to cause the current controller to also vary the electric current to scan the electrons orthogonally to the steering angle to reduce a dose density on the vacuum window.

9. The system of claim 1 wherein the electromagnet is housed within the vacuum chamber.

10. The system of claim 1 wherein the electromagnet is located outside the vacuum chamber.

11. The system of claim 1 further comprising an x-ray converter plate located between the electromagnet and the product to intercept electrons steered from the vacuum chamber toward the product.

* * * * *